United States Patent
Mansfield et al.

(10) Patent No.: US 7,289,835 B2
(45) Date of Patent: Oct. 30, 2007

(54) MULTIVARIATE ANALYSIS OF GREEN TO ULTRAVIOLET SPECTRA OF CELL AND TISSUE SAMPLES

(75) Inventors: James Mansfield, Boston, MA (US); Jenny Freeman, Weston, MA (US)

(73) Assignee: Masimo Laboratories, Inc., Irvine, CA (US)

( * ) Notice: Subject to any disclaimer, the term of this patent is extended or adjusted under 35 U.S.C. 154(b) by 0 days.

(21) Appl. No.: 11/145,342

(22) Filed: Jun. 2, 2005

(65) Prior Publication Data

US 2005/0222501 A1 Oct. 6, 2005

Related U.S. Application Data

(63) Continuation of application No. 10/638,656, filed on Aug. 11, 2003, now abandoned, which is a continuation of application No. 09/785,531, filed on Feb. 20, 2001, now abandoned.

(60) Provisional application No. 60/183,356, filed on Feb. 18, 2000.

(51) Int. Cl.
*A61B 5/00* (2006.01)
(52) U.S. Cl. ...................... 600/316; 600/317
(58) Field of Classification Search ................ 600/310, 600/316, 317, 476; 356/317; 250/341.1
See application file for complete search history.

(56) References Cited

U.S. PATENT DOCUMENTS

| | | | | |
|---|---|---|---|---|
| 5,576,544 A | * | 11/1996 | Rosenthal | 250/341.1 |
| 5,725,480 A | * | 3/1998 | Oosta et al. | 600/310 |
| 6,232,609 B1 | * | 5/2001 | Snyder et al. | 250/461.1 |
| 6,280,381 B1 | * | 8/2001 | Malin et al. | 600/322 |

\* cited by examiner

*Primary Examiner*—Eric F Winakur
(74) *Attorney, Agent, or Firm*—Knobbe, Martens, Olson & Bear, LLP

(57) ABSTRACT

This invention relates to methods for processing in vivo skin auto-fluorescence spectra for determining blood glucose levels. The invention also relates to methods of classifying cells or tissue samples or quantifying a component of a cell or tissue using a multivariate classification or quantification model.

2 Claims, No Drawings

MULTIVARIATE ANALYSIS OF GREEN TO ULTRAVIOLET SPECTRA OF CELL AND TISSUE SAMPLES

RELATED APPLICATION

The present invention is a continuation of U.S. patent application Ser. No. 10/638,656, filed Aug. 11, 2003 now abandoned, which is a Continuation of U.S. patent application Ser. No. 09/785,531, filed Feb. 20, 2001, now abandoned, which claims the benefit of U.S. Provisional Patent Application No. 60/183,356, filed Feb. 18, 2000, and titled "Multivariate Analysis of Green to Ultraviolet Spectra of Cell and Tissue Samples", now abandoned.

BACKGROUND OF THE INVENTION

1. Field of the Invention

This invention relates to analysis methodology and multivariate classification of diagnostic spectra, and, in particular, to methods for processing in vivo skin auto-fluorescence spectra for determining blood glucose levels. The invention also relates to methods of classifying cells or tissue samples or quantifying a component of a cell or tissue using a multivariate classification or quantification model.

2. Description of the Background

Near-IR spectra taken from agricultural samples, such as grains, oil, seeds and feeds, etc., have been used to quantitate various bulk constituents, e.g., total protein, water content, or fat content. See, P. Williams et al., "Agricultural Applications of Near-IR Spectroscopy and PLS Processing," Canadian Grain Commission.

Multivariate statistical methods have long been used in the analysis of biomedical samples by infrared and near infrared, generally under the name "chemometrics." See, U.S. Pat. No. 5,596,992 to Haaland et al., titled "Multivariate Classification of Infrared Spectra of Cell and Tissue Samples," and U.S. Pat. No. 5,857,462 to Thomas et al., titled "Systematic Wavelength Selection For Improved Multivariate Spectral Analysis."

The use of multivariate methods for the analysis of ex vivo tissue samples is well established. For spectra taken in vivo, some work has been done. Linear discriminant analysis has been used to classify visible/near-IR spectra of human finger joints into early and late rheumatoid arthritis classes. Multivariate methods have been used to classify fluorescence spectra taken in vivo from cervixes according to the presence or absence of cervical cancer or pre-cancerous tissues.

In general, the field of chemometrics is well established, and the use of multivariate statistical methods for the analysis of complex spectra is common. These methods are used in pharmaceutical analysis, industrial applications, and, more recently, biomedical spectral analysis.

SUMMARY OF THE INVENTION

Recently, it has been discovered that glucose levels can be determined in vivo by measuring fluorescence spectra emitted from the skin surface following excitation with one or more wavelengths. See, U.S. patent application Ser. No. 09/287,486, titled, "Non-Invasive Tissue Glucose Level Monitoring," filed Apr. 6, 1999, and incorporated in its entirety herein by reference. Particularly, peak ratios, correlation analysis, and linear regression analysis have been used to analyze skin autofluorescence spectra for the purpose of determining the blood glucose concentration. Partial least squares ("PLS") analysis of near-IR spectra is the basis of all infrared efforts towards non-invasive glucose monitoring.

Analysis of collected spectra is complicated by the fact that it can be difficult to distinguish changes or variations in the spectra due to skin variables, such as skin inhomogeneity, UV damage, age, erythema, and the like. The present invention addresses this problem by providing a method of processing in vivo skin auto fluorescence spectra to account for these types of variables.

Accordingly, one embodiment of the invention is directed to a method for processing in vivo skin auto fluorescence spectra emitted by a skin surface of a patient to determine a blood glucose level of the patient. The method comprises the steps of collecting auto fluorescent spectra emitted from the skin surface of the patient, and correcting the collected spectra using multivariate analysis techniques to account for variables among skin surfaces.

Another embodiment is directed to an instrument for determining a correct glucose level of a patient by measuring in vivo auto-fluorescence of the patient's skin comprising: means for irradiating the skin with a plurality of excitation wavelengths; means for collecting a plurality of emitted wavelengths; and means for analyzing the collected wavelengths to determine a preliminary blood glucose level. The means for analyzing comprises a means for correcting the preliminary blood glucose level to account for variations in skin using one or more multivariate analytical techniques to determine the correct glucose level of the patient.

In addition, the present invention also relates to methods of classifying cells or tissue samples, or quantifying their components, using multivariate analysis of the measured intensities of a plurality of wavelengths of emitted radiation.

Other embodiments and advantages of the invention are set forth in part in the description which follows, and in part, will be obvious from this description, or may be learned from the practice of the invention.

DESCRIPTION OF THE INVENTION

As embodied and broadly described herein, the present invention is directed to the processing of in vivo skin auto-fluorescence spectra for the purposes of determining blood glucose levels. In-vivo fluorescence spectra have been shown to correlate with blood glucose levels. See, Id. Although large changes in skin fluorescence spectra due to changes in blood glucose levels have been observed, it can sometimes be difficult to separate the variations in the spectra caused by changes in blood glucose from other spectral changes due to factors such as skin inhomogeneity, age effects, UV damage, erythema, etc.

For large subject populations, it is desirable to be able to determine an algorithm for converting skin fluorescence spectra into glucose values which works on a large percentage of the population as opposed to a single individual. Thus, there is a need for an analysis method that takes into account more spectral information than that which is found at a single wavelength or two.

By analyzing large numbers of spectra from a wide range of individuals, a useful instrument for the non-invasive monitoring of glucose using fluorescence excitation spectroscopy may be developed which accommodates differences in skin. By using multivariate statistical approaches, a quantitation algorithm useful across many individuals may be created. Many multivariate techniques are useful in this regard. Useful analytical methodologies include, but are not limited to: quantification methodologies, such as, partial least squares, principal component regression ("PCR"), linear regression, multiple linear regression, stepwise linear regression, ridge regression, radial basis functions, and the like; classification methodologies, such as, linear discriminant analysis ("LDA"), cluster analysis (e.g., k-means, C-means, etc., both fuzzy and hard), neural network ("NN") analysis; and data processing methodologies, such as, 1-D or 2-D smoothing filters (based on median filtering, mean filtering, discrete cosine, wavelet, or Fourier transform), Laplacian operators, maximum likelihood estimators, maximum entropy methods, first and second derivatives (both in 1-D and 2-D implementations), peak enhancement methods (such as Fourier self-deconvolution), principal components analysis as a pre-processing step, and varimax rotations for PLS and PC methods.

Other methodologies and data processing methods may further include sorting data according to their glucose values, followed by the application of one or more data filtering/smoothing algorithms, within an individual in a small dataset or within each individual for larger, multiple-person datasets. Sorting by glucose or any other relevant analyte has at least two desirable effects: (1) it groups data with similar glucose values together, so that the subsequent application of filtering techniques will reduce "noise" not attributable to glucose, and (2) it reduces temporal correlation inherent in preserving a dataset as a time series, and thereby reduces, spurious correlation effects.

In addition or alternately, spectral transformation algorithms may be applied to each person's data prior to smoothing or sorting. These transfer functions will enable calibrations made on spectra from one individual to be more easily transferable to spectra from another individual or individuals by minimizing the spectral differences between them. Such algorithms may be as simple as the ratio of the means of the spectra of two individuals, or some complex algorithm which takes into account the responsivity characteristics of each spectrometer.

Methods of the invention may also include pre-classification of spectra into categories of glucose levels prior to quantification. This can be done with any of the supervised classification methods listed above, e.g., LDA, PCR, NN, and the like. Sequential binary division of spectra may also be applied, e.g., above/below 150 then, if below 150, above/below 100, if above 150, then above/below 200, etc.

Furthermore, non-linear model fitting techniques can be used to incorporate prior models of absorption and emission spectra of known fluorophores, and subsequently use the parameters of the best fit model as part of the multivariate analysis.

In addition, methods of the invention may also use wavelength-selection algorithms to reduce the number of spectral data points prior to classification or quantitation. Examples of these methods include genetic algorithm methodologies, step-wise linear regression and comprehensive combinatorial linear discriminant analysis, and the like.

Accordingly, one embodiment of the invention is directed to a method for processing in vivo skin auto fluorescence spectra emitted by a skin surface of a patient to determine a blood glucose level of the patient comprising the steps of collecting auto fluorescence spectra emitted from, the skin surface of the patient and correcting the collected spectra using multivariate analysis methods to account for variables among skin surfaces. The multivariate analysis method may comprise one or more quantification, classification or data processing methods selected from the group consisting of partial least squares, principal component regression, linear regression, multiple linear regression, stepwise linear regression, ridge regression, linear discriminant analysis, cluster analysis (k-means, C-means, etc., both fuzzy and hard), neural network analysis, smoothing filters (based on median filtering, mean filtering, discrete cosine, wavelet and Fourier transform smoothing all in both 1-D and 2-D methods), laplacian operators, maximum likelihood estimators, maximum entropy methods, first and second derivatives (both in 1-D and 2-D implementations), peak enhancement methods such as Fourier self-deconvolution, principal components analysis as a pre-processing step, and varimax rotations for PLS and PC methods.

Another embodiment is directed to an instrument for determining a correct glucose level of a patient by measuring in vivo auto-fluorescence of the patient's skin comprising: means for irradiating the skin with a plurality of excitation wavelengths; means for collecting a plurality of emitted wavelengths; and means for analyzing the collected wavelengths to determine a preliminary blood glucose level. The means for analyzing comprising means for correcting the preliminary blood glucose level to account for variations in skin. The means for correcting comprising using one or more multivariate analytical methodologies to determine the correct glucose level of the patient.

Quantification Models

The present invention is useful for quantifying components in a cell or tissue, and may be used, for example, to quantify tissue glucose levels in vivo. Accordingly, one embodiment of the invention is directed to a method of quantifying a component of a cell or tissue sample comprising the steps of: generating a single excitation wavelength or plurality of different excitation wavelengths of green to ultraviolet light; irradiating the sample with the light and measuring the intensity of the stimulated emission of the sample at a minimum of three different wavelengths of lower energy than the excitation light or at a plurality of wavelengths of lower energy than the excitation light; and quantifying one or more components of the cell or tissue from the measured intensities by using a multivariate quantification model. The green to ultraviolet light may be in the green to violet range of wavelengths, or alternately, it may be in the violet to near-ultraviolet range of wavelengths.

The component quantified may be glucose or another desired component. Irradiating may be done in vivo or in vitro.

In a preferred embodiment, the step of quantifying the component of the sample includes at least one spectral data pre-processing step. In one such embodiment, the pre-processing step includes at least one of the steps of selecting wavelengths, correcting for a linear baseline, and normalizing a spectral region surrounding the different wavelengths, used for classification of one spectral band in that spectral region. Alternately, the preprocessing step includes at least one of the steps of normalizing for total area of the spectrum, filtering or smoothing the data, or pre-sorting by analyte.

Multivariate quantification may be done by a partial least squares technique, by a principal component regression technique, or by one of multiple linear regression, stepwise linear regression or ridge regression.

In a preferred embodiment of this method, the step of quantifying the component of the sample is performed by a multivariate algorithm using the measured intensity information and at least one multivariate quantification model which is a function of conventionally determined cell or tissue component quantities from a set of reference samples and a set of spectral intensities as a function of wavelength obtained from irradiating the set of reference samples with green to ultraviolet light and monitoring the stimulated emission.

Another embodiment of the invention is directed to a method of quantifying a component of a cell or tissue sample comprising: generating a single excitation wavelength or plurality of different excitation wavelengths of mid-ultraviolet light; irradiating the sample with said light and measuring the intensity of the stimulated emission of the sample at a minimum of three different wavelengths of lower energy than the excitation light or at a plurality of wavelengths of lower energy than the excitation light; generating at least one multivariate quantification model, said model quantifying the different components of the sample as a function of the intensity characteristics at the measured wavelengths in relation to a reference quantitation result; calculating the quantity of the component from the measured intensities by using multivariate quantitation of the intensities at the at least three different wavelengths based on the quantitation model; and quantifying the component from the measured intensities by using said multivariate quantification model.

As with the previous embodiment, the sample component may be quantified in vitro or in vivo. Components which may be analyzed include glucose.

Preferably, the step of quantifying the component of the samples includes at least one spectral data pre-processing step. The pre-processing step preferably includes at least one of the steps of selecting wavelengths, correcting for a linear baseline, and normalizing a spectral region surrounding the different wavelengths, used for classification of one spectral band in that spectral region. Alternately, the preprocessing step includes at least one of the steps of normalizing for total area of the spectrum, filtering or smoothing the data, or pre-sorting the data by analyte. Multivariate quantification may be done by a partial least squares technique, by a principal component regression technique, or by one of multiple linear regression, stepwise linear regression or ridge regression.

In a preferred embodiment, the step of quantifying the component of the sample is performed by a multivariate algorithm using the measured intensity information and at least one multivariate quantification model which is a function of conventionally determined cell or tissue component quantities from a set of reference samples and a set of spectral intensities as a function of wavelength obtained from irradiating the set of reference samples with green to ultraviolet light and monitoring the stimulated emission.

The present invention is also directed to a system for quantifying one or more components of a cell or tissue sample comprising: means for generating a single excitation wavelength or a plurality of different excitation wavelengths of green to ultraviolet light; means for directing at least a portion of the green to ultraviolet light into the sample; means for collecting at least a portion of the stimulated emission light after the excitation light has interacted with the sample; means for measuring an intensity of the collected stimulated emission light at least three different wavelengths; means, coupled to the measuring means, for storing the measured intensities as a function of the wavelength; means for storing at least one multivariate quantification model which contains data indicative of a correct quantification of components of known cell or tissue samples; and processor means coupled to the means for storing the measured intensities and the means for storing the model, the processor means serving as means for calculating the quantity of the components of the cell or tissue sample by use of the multivariate quantification model and the measured intensities.

In one embodiment of the system, the means to direct the light and the means to collect the light comprise an endoscope. Alternately, the means to direct the light and the means to collect the light may comprise a fiber optic bundle. The system may further include means to determine outliers.

Classification Models

The present invention may also be used to classify cells or tissue samples. For example, one such embodiment is directed to a method of classifying a cell or tissue sample comprising the steps of: generating a single excitation wavelength or plurality of different excitation wavelengths of green to ultraviolet light; irradiating the sample with said light and measuring the intensity of the stimulated emission of the sample at a minimum of three different wavelengths of lower energy than the excitation light or at a plurality of wavelengths of lower energy than the excitation light; and classifying the sample as one of two or more cell or tissue types from the measured intensities by using a multivariate classification model.

The green to ultraviolet light may be in the green to violet range of wavelengths, or alternately, in the violet to near-ultraviolet range of wavelengths.

The sample may be classified as normal or abnormal. Irradiating may be done in vivo or in vitro.

Preferably, the step of classifying the samples includes at least one spectral data pre-processing step. For example, the pre-processing step may include at least one of the steps of selecting wavelengths, correcting for a linear baseline, and normalizing a spectral region surrounding the different wavelengths, used for classification of one spectral band in that spectral region. Alternately, the pre-processing step may include at least one of the steps of normalizing for total area of the spectrum, filtering or smoothing the data, or pre-sorting the data by analyte.

Multivariate classification may be done by a linear discriminant analysis technique. Preferably, the linear discriminant analysis is preceded by a principal component analyzing step limiting the number of discriminant variables.

In a preferred embodiment of the method, the step of classifying the sample is performed by a multivariate algorithm using the measured intensity information and at least one multivariate classification model which is a function of conventionally determined cell or tissue sample classes from a set of reference samples and a set of spectral intensities as a function of wavelength obtained from irradiating the set of reference samples with green to ultraviolet light and monitoring the stimulated emission.

Another embodiment of the invention is directed to a method of classifying a cell or tissue sample comprising: generating a single excitation wavelength or plurality of different excitation wavelengths of mid-ultraviolet light; irradiating the sample with said light and measuring the intensity of the stimulated emission of the sample at a minimum of three different wavelengths of lower energy than the excitation light or at a plurality of wavelengths of lower energy than the excitation light; generating at least one multivariate classification model, said model classifying the sample as a function of the intensity characteristics at the measured wavelengths in relation to a reference classification; calculating the classification of the sample from the measured intensities by using multivariate classification of the intensities at the at least three different wavelengths based on the classification model; and classifying the sample as one of two or more cell or tissue types from the measured intensities by using said multivariate classification model.

Classifying may be done in vitro or in vivo. The sample may be classified as normal or abnormal. Preferably, the step of classifying of the samples includes at least one spectral data pre-processing step. For example, the pre-processing step may include at least one of the steps of selecting wavelengths, correcting for a linear baseline, and normalizing a spectral region surrounding the different wavelengths, used for classification of one spectral band in that spectral region. Alternately, the pre-processing step may include at least one of the steps of normalizing for total area of the spectrum, filtering or smoothing the data, or pre-sorting the data by analyte.

In one embodiment, multivariate classification is done by a linear discriminant analysis technique. In this embodiment, the linear discriminant analysis is preferably preceded by a principal component analyzing step limiting the number of discriminant variables.

In a preferred embodiment of this method, the step of classifying the sample is performed by a multivariate algorithm using the measured intensity information and at least one multivariate classification model which is a function of conventionally determined cell or tissue sample classes from a set of reference samples and a set of spectral intensities as a function of wavelength obtained from irradiating the set of reference samples with green to ultraviolet light and monitoring the stimulated emission.

Another embodiment is directed to a system for classifying cell or tissue samples comprising: means for generating a single excitation wavelength or a plurality of different excitation wavelengths of green to ultraviolet light; means for directing at least a portion of the green to ultraviolet light into the samples; means for collecting at least a portion of the stimulated emission light after the excitation light has interacted with the samples; means for measuring an intensity of the collected stimulated emission light at least three different wavelengths; means, coupled to the measuring means, for storing the measured intensities as a function of the wavelength; means for storing at least one multivariate classification model which contains data indicative of a correct classification of known cell or tissue samples; and processor means coupled to the means for storing the measured intensities and the means for storing the model, the processor means serving as means for calculating the classification of the cell or tissue samples as one of two or more cells or tissues by use of the multivariate classification model and the measured intensities.

In one embodiment, the means to direct the light and the means to collect the light comprise an endoscope. Alternately, the means to direct the light and the means to collect the light comprises a fiber optic bundle. The system may further include means to determine outliers.

In the above embodiments, the means for generating excitation radiation may be any type of excitation source, preferably, xenon arc lamps (plus appropriate filters and/or monochromators); a plurality of laser diodes or LEDs; mercury lamps; halogen lamps; tungsten filament lamps; or any combination thereof. Further, appropriate filters and/or monochromators can be added.

In addition to using a fiber optic bundle or endoscope, suitable means for directing or collecting radiation may comprise any of the following: liquid light guides; system of optical components (mirrors, lenses, etc.); individual fiber optic cables; plastic optical components; quartz optical components; or any combination thereof.

In the above embodiments, suitable means for measuring an intensity of the radiation may be selected form the group consisting of photodiodes; photodiode arrays; avalance photodiodes; LEDs; laser diodes; charge couple device (CCD) detectors (arrays or individually); silicon detectors; or any combination thereof. Suitable storing means may be computers (hardware and software); EPROMs; programmed firmware; and the like. Further, suitable processing means may be any type of existing digital processing devices.

Other embodiments and uses of the invention will be apparent to those skilled in the art from consideration of the specification and practice of the invention disclosed herein. All references cited herein, including all U.S. and foreign patents and patent applications, are specifically and entirely hereby incorporated herein by reference, including, but not limited to, U.S. patent application Ser. No. 09/287,486, titled "Non-Invasive Tissue Glucose Level Monitoring," filed Apr. 6, 1999. U.S. Patent Application titled "Reduction of Inter-Subject Variation Via Transfer Standardization," U.S. Patent Application titled "Generation of Spatially-Averaged Excitation-Emission Map in Heterogeneous Tissue," and U.S. Patent Application titled "Non-Invasive Tissue Glucose Level Monitoring," all filed contemporaneously herewith, are entirely and specifically incorporated by reference. It is intended that the specification and examples be considered exemplary only, with the true scope and spirit of the invention indicated by the following claims.

The invention claimed is:

1. A method for processing in vivo skin auto fluorescence spectra emitted by a skin surface of a patient to determine a blood glucose level of the patient comprising the steps of:
    collecting clinical fluorescence spectra data and corresponding glucose values from a range of individuals, said spectra data responsive to irradiation of tissue at a plurality of wavelengths of energy;
    sorting said clinical fluorescence spectra data according to said glucose values;
    processing said sorted clinical fluorescence spectra data to reduce effects of noise;
    collecting fluorescence spectra data emitted from the skin surface of the patient;
    correcting the collected spectra data using multivariate analysis to account for skin surface variables; and
    determining a blood glucose level of the patient based on at least said corrected spectra data and said processed clinical fluorescence spectra data.

2. The method of claim 1 wherein the multivariate analysis comprises one or more quantification, classification, or data processing techniques including: partial least squares, principal component regression, linear regression, multiple linear regression, stepwise linear regression, ridge regression, radial basis functions, linear discriminant analysis, cluster analysis, neural network analysis, smoothing filters, laplacian operators, maximum likelihood estimators, maximum entropy, first and second derivatives, peak enhancement, Fourier self-deconvolution, principal components, and varimax rotations.

* * * * *